US00PP09221P

United States Patent [19]

DeRoose

[11] Patent Number: Plant 9,221

[45] Date of Patent: Jul. 25, 1995

[54] CORDYLINE PLANT NAMED 'KATRIJN'

[76] Inventor: Reginald DeRoose, Drootge 139,, 9940 Evergem, Belgium

[21] Appl. No.: 310,476

[22] Filed: Sep. 22, 1994

[51] Int. Cl.[6] ..... A01H 5/00
[52] U.S. Cl. ..... Plt./88.8
[58] Field of Search ..... Plt. 88.8

[56] References Cited

PUBLICATIONS

Bailey, L. H., "Cordyline", *Hortus Third,* 1976, Macmillan Publishing Co., Inc., N.Y. p. 312.

*Primary Examiner*—James R. Feyrer
*Attorney, Agent, or Firm*—Foley & Lardner

[57] ABSTRACT

A Cordyline plant named Katrijn, primarily characterized by its uniquely variegated leaves. Young leaves are of yellow-green variegation with an ivory-white margin and pink edge. As the leaves mature, the green becomes darker and the stripes change mainly to medium to dark red-purple with some pink. Between young and mature leaves, the color variation is striking.

1 Drawing Sheet

The present invention comprises a new and distinct cultivar of Cordyline plant, botanically known as *Cordyline fruticosa,* and referred to by the cultivar name Katrijn.

Katrijn is a spontaneous mutation discovered by the inventor Reginald Deroose in 1987 in a greenhouse in Evergem, Belgium. The new cultivar was discovered growing among plants of the parent cultivar Kiwi, a commercial but unpatented cultivar having yellow-green variegated leaves with a dark red to dark pink margin. The new cultivar was immediately recognized by its uniquely variegated leaves, having distinct colors ranging from green to pink and purple, with ivory-white margins and pink edges.

Subsequent asexual reproduction of the new cultivar by cuttings, performed by the inventor in Evergem, Belgium, has demonstrated that the combination of characteristics as herein disclosed for the new cultivar are firmly fixed and are retained through successive generations of asexual reproduction.

The following traits have been repeatedly observed and in combination distinguish Katrijn as a new and distinct cultivar:

1. Katrijn has a single main stem, with all leaves being located opposite to each other.
2. Short internodes.
3. The leaf stems are grooved.
4. Leaves are oblong to lanceolate. The tips of the leaves bend down and the margins are wavy.
5. The variegated leaves have distinct colors ranging from green to pink and purple, with ivory-white margins and pink edges. Young leaves have primarily green variegation, with narrow pink striations or strips. As the leaves mature, the green becomes darker and eventually becomes mainly pink and various shades of medium to dark red-purple.

In comparison to the parent cultivar and other known cultivars, Katrijn is primarily distinguished by its purple/pink variegated mature leaves. As above noted, young leaves have more green variegation, but as the leaves mature, the green changes primarily to medium to dark purple-red with striations or stripes of pink. The display of young and mature leaves of the entire spectrum of variegated colors is unique. The leaves of the parent cultivar kiwi are variegated yellow-green, with a dark pink to dark red margin, and older leaves of kiwi have essentially the same variegation colors as young leaves.

The accompanying color photographs show the unique features of the new cultivar, with colors being as accurate as possible with illustrations of this type. The top photo is a top perspective view of an entire plant, clearly showing the variegation patterns of young and mature leaves. The photo on the bottom is a close-up view showing the variegation colors in more detail.

The following observations, measurements and values describe plants grown in Evergem, Belgium under greenhouse conditions which closely approximate those generally used in horticultural practice. Color references are made to The Royal Horticultural Society (R.H.S.) Colour Chart, except where general color terms of ordinary significance are used. The color values were determined between 10 a.m. and noon in Aug. 1992 under slightly clouded but bright daylight conditions.

Origin: Mutation of *Cordyline fruticosa* Kiwi.
Classification: *Cordyline fruticosa* cv Katrijn.
Propagation: By cuttings.
Plant: The plant has the usual *Cordyline fruticosa* shape. The plant has a main stem with leaves opposite to each other. The stem has short internodes, about 1.5 to 2 cm. The leaves are at an angle of about 30° to the main stem. The leaves are arching-recurved and the leaf tips bend down.
Leaves:
- *Form.*—Oblong to lanceolate with tips bending down.
- *Size.*—22 cm long and 5 cm wide.
- *Margin.*—Smooth and wavy.
- *Aspect.*—Surface is slightly wavy.
- *Texture.*—Mat to glossy.
- *Leaf stem.*—About 7.5 cm long; width varies from 8 mm to at bottom to 4 mm at top.

*Veins.*—Thick midrib with normal side veins extending from the midrib and following the length of the leave.

*Variegation.*—Irregular striping along the leaf in green, ivory, pink and purple.

*Color.*—Upper surface: Young leaves have an ivory white margin approximately 11C with a pink 54A edge, stripes of green 145A, 146A and 147A, and stripes of yellow 8A. When the leaves mature, the green stripes are more 147A and 189 A. When mature, the striping changes to mainly pink and purple 59C, 54A and 70A. The margin remains ivory white 11C with a trace of pink, and the edge pink 54A. Lower Surface: Green approximatley 189A with very visible side veins 70A in color, and ivory white 11C margins with a trace of pink, and the edge pink 54A. Upper surface midrib: Youngest leaves green 147A; older leaves 54A to 70A. Lower surface midrib: 70A. Leafstem: Middle about R.H.S. 200A, the edges 54A.

Inflorescence: Not significant.

Roots: Normal, white.

It is claimed:

1. A new and distinct cultivar of Cordyline plant named Katrijn, as illustrated and described.

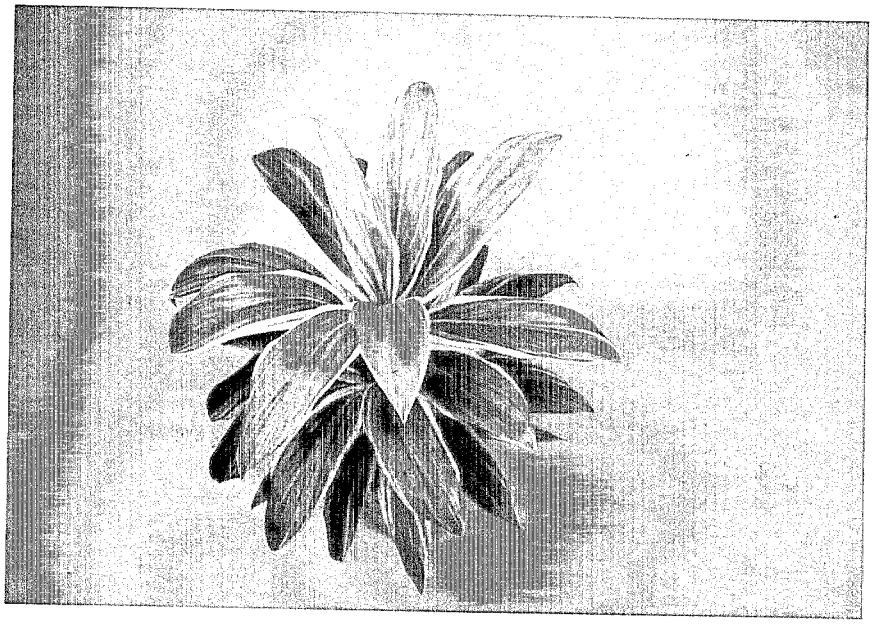
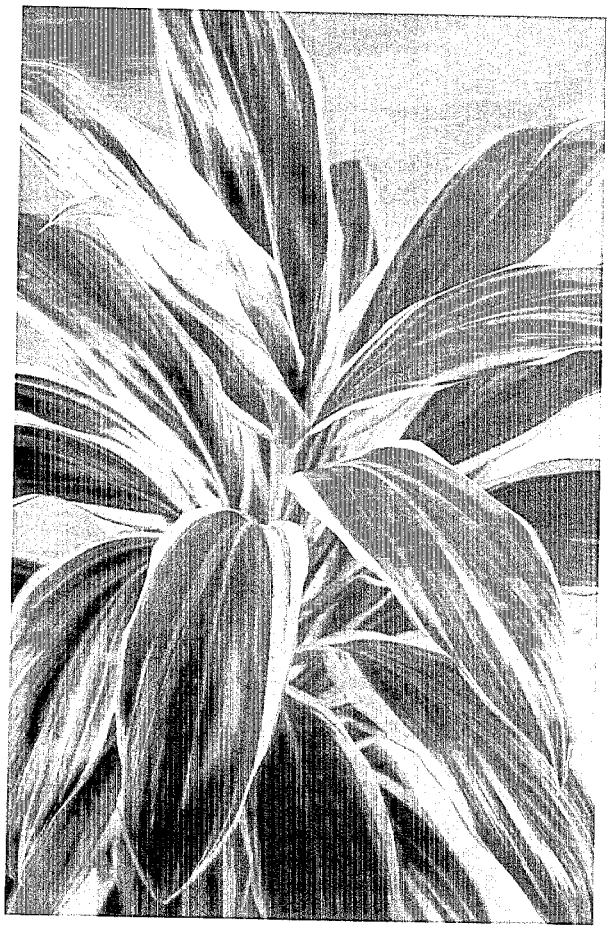

* * * * *